United States Patent [19]
Hersh

[11] Patent Number: 6,030,226
[45] Date of Patent: Feb. 29, 2000

[54] APPLICATION OF MULTI-MEDIA TECHNOLOGY TO PSYCHOLOGICAL AND EDUCATIONAL ASSESSMENT TOOLS

[76] Inventor: Michael Hersh, 817-A Ave. M, Brooklyn, N.Y. 11230

[21] Appl. No.: 08/829,488

[22] Filed: Mar. 27, 1997

Related U.S. Application Data

[60] Provisional application No. 60/014,203, Mar. 27, 1996.

[51] Int. Cl.[7] .................................................. G09B 19/00
[52] U.S. Cl. ............................................ 434/236; 434/156
[58] Field of Search ................................... 434/118, 156, 434/157, 185, 307 R, 308, 322, 323, 362, 236–238

[56] References Cited

U.S. PATENT DOCUMENTS

| | | | |
|---|---|---|---|
| H1452 | 6/1995 | Kennedy | 434/322 |
| 3,390,397 | 6/1968 | Friedlander | 346/33 |
| 3,808,705 | 5/1974 | Schmoyer | 35/6 |
| 4,234,933 | 11/1980 | Adelson | 364/900 |
| 4,375,080 | 2/1983 | Barry | 364/551 |
| 4,490,810 | 12/1984 | Hon | 364/900 |
| 4,684,349 | 8/1987 | Ferguson | 434/308 |
| 4,690,644 | 9/1987 | Flanders | 434/158 |
| 4,690,645 | 9/1987 | Ukisu | 434/309 |
| 4,760,390 | 7/1988 | Maine | 340/747 |
| 4,770,636 | 9/1988 | Buschke | 434/236 |
| 4,793,810 | 12/1988 | Beasley | 434/165 |
| 4,810,197 | 3/1989 | Hicks | 434/281 |
| 4,839,822 | 6/1989 | Dormond | 364/513 |
| 4,895,518 | 1/1990 | Arnold | 434/118 |
| 5,017,142 | 5/1991 | Bemis | 434/220 |
| 5,100,329 | 3/1992 | Deesen | 434/327 |
| 5,102,341 | 4/1992 | Koslin | 434/353 |
| 5,120,230 | 6/1992 | Clark | 434/307 |
| 5,173,051 | 12/1992 | May | 434/118 |
| 5,202,952 | 4/1993 | Gillick | 395/2 |
| 5,204,813 | 4/1993 | Samph | 364/419 |
| 5,211,564 | 5/1993 | Martinez | 434/323 |
| 5,226,819 | 7/1993 | Takagaki | 434/236 |
| 5,240,419 | 8/1993 | deGyarfas | 434/322 |

(List continued on next page.)

*Primary Examiner*—Robert A. Hafer
*Assistant Examiner*—John Edmund Rovnak
*Attorney, Agent, or Firm*—Alfred M. Walker

[57] ABSTRACT

Multi-media technology is applied to the testing of children, brain damaged adults and the general population using standard psychological and educational assessment tools. To avoid the inherent bias occurring when a tester speaks in a language or dialect not fully comprehended by the student or other human subject, the multi-media computer has a linguistic adaptation means, such as a sound card and data associated therewith, which can produce sounds, such as test instructions, in the most appropriate language and dialect of the test taker, such as a student, so that the human tester can provide the human subject with instructions for responding to the psychological evaluation. The human subject is exposed to computer-generated multi-media psychological evaluative probing, so that the human subject can respond to the computer-generated psychological evaluative probing. The computer tallies and records the student's responses and analyzes the human subject's recorded responses. Afterward the computer automatically prepares a report based upon the human subject's recorded responses, and transfers its report, such as transfer to a computer-readable diskette or by printing to a printer.

26 Claims, 14 Drawing Sheets

U.S. PATENT DOCUMENTS

| | | | |
|---|---|---|---|
| 5,241,671 | 8/1993 | Reed | 395/600 |
| 5,261,823 | 11/1993 | Kurokawa | 434/323 |
| 5,267,865 | 12/1993 | Lee | 434/350 |
| 5,275,569 | 1/1994 | Watkins | 434/157 |
| 5,287,489 | 2/1994 | Nimmo | 395/500 |
| 5,302,132 | 4/1994 | Corder | 434/156 |
| 5,318,450 | 6/1994 | Carver | 434/336 |
| 5,344,324 | 9/1994 | O'Donnell | 434/258 |
| 5,344,326 | 9/1994 | Ferris | 434/336 |
| 5,379,213 | 1/1995 | Derks | 364/411 |
| 5,437,553 | 8/1995 | Collins | 434/322 |
| 5,447,166 | 9/1995 | Gevins | 128/731 |
| 5,454,721 | 10/1995 | Kuch | 434/127 |
| 5,456,607 | 10/1995 | Antoniak | 434/323 |
| 5,473,744 | 12/1995 | Allen | 395/154 |
| 5,483,468 | 1/1996 | Chen | 364/551.01 |
| 5,496,175 | 3/1996 | Oyama | 434/118 |
| 5,511,982 | 4/1996 | Pigache | 434/350 |
| 5,551,880 | 9/1996 | Bonnstetter et al. | 434/236 |
| 5,671,409 | 9/1997 | Fatseas et al. | 395/615 |
| 5,676,551 | 10/1997 | Knight et al. | 434/236 |
| 5,696,981 | 12/1997 | Shovers | 395/760 |
| 5,711,671 | 1/1998 | Geeslin et al. | 434/236 |
| 5,828,943 | 10/1998 | Brown | 434/258 |
| 5,882,203 | 3/1999 | Correa et al. | 434/236 |

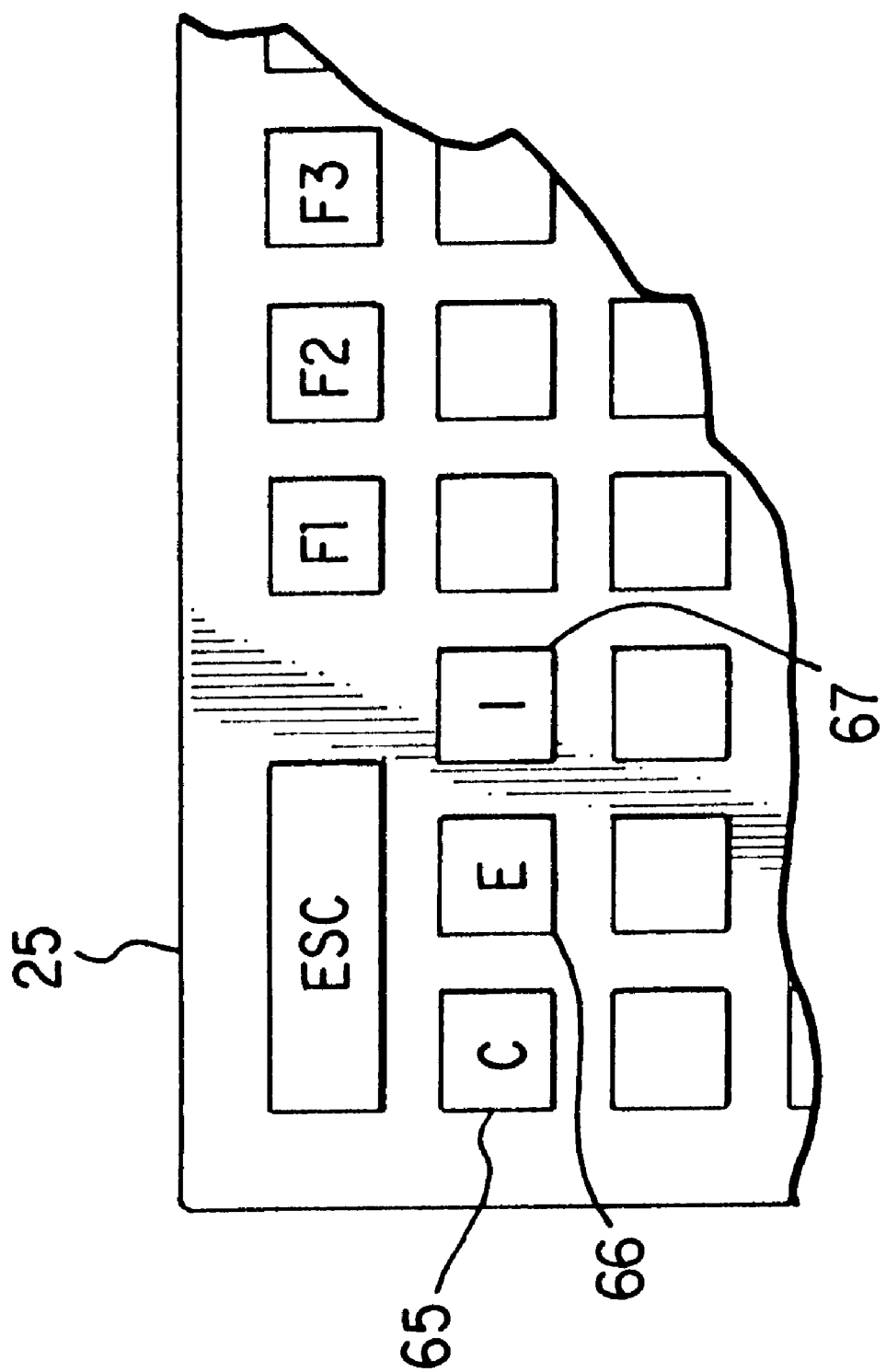

APPLICATION OF MULTI-MEDIA TECHNOLOGY TO PSYCHOLOGICAL AND EDUCATIONAL ASSESSMENT TOOLS

This application is based on Provisional Application Ser. No. 60/014,203, filed on Mar. 27, 1996.

FIELD OF THE INVENTION

This invention is related to interactive multi-media applications in psychological testing.

BACKGROUND OF THE INVENTION

Psychological and educational assessment tools have been used for the measurement and evaluation of abilities, aptitudes, personality characteristics and so forth. An early example of such tests dates back to 1904 when psychologist Alfred Binet was asked by the French Ministry of Education to design a test that would identify slow learners. It was noted that some children did not learn well in an ordinary classroom setting and needed special help. Reluctant to let teachers identify slow learners due to the possibility of prejudicial bias, an objective test was sought that would reveal who could benefit from remedial work. Binet's brainstorm was the famous IQ test.

It is well to note the basic difference between the assessment tools that are the subject of this invention and the skill acquisition or remedial training tools commonly known as computer-assisted instruction (CAI). Many examples of the latter courseware for simple presentation or the newer multi-media versions are available in subjects from art to zoology. The main attribute of such courseware (including testing) is the interactive nature of the programs and the convenience and "customizing" of each session as a function of the demonstrated skill level of the student. In CAI the notions of reliability, validity, bias, and standardization are seldom of central importance because of the objective nature of the courseware.

These notions, however, are of primary importance in the psychological and educational assessment tools; furthermore, accurate determination of the subject's basals and ceilings is required for the proper administration and scoring of the test.

The allocation of presentation material to video vs. audio is just a matter of style or perceived effectiveness in the CAI environment. The situation is quite different regarding assessment tools which are rigorously field tested (ie. "normed") for reliability and validity; the mode of administration is precisely stipulated, and any deviation may violate the conditions under which it had been normed. For psychological and educational assessment tools, the full range of multi-media presentation features closely simulates the manual version of a normed test. The standards used to create the manual test are easily translated to the computer test by a comparative study of the similarity of test scores of computer assisted versus manual testing.

To summarize the distinctions between CAI and norm referenced computer-assisted assessment (CAA) of the present invention, the uses of each as well as the scoring techniques should be explored. CAI is used to teach new material, to review learned material as in drill and practice, to teach productivity techniques such as word processing and to teach programming. Some CAI programs have features to keep track of scores or to adjust the level of difficulty. In contrast, CAA of the present invention is an assessment tool; teaching is not the objective. Scoring of CAA is sophisticated with raw scores, standard scores, subtests, age equivalents, and basals and ceilings. The testing rules of CAA are rigid with no deviation allowed.

The traditional psychological and educational assessment manual tools are usually administered one-on-one with a clinician serving the dual role of test administrator and observer/recorder. For brain damaged adults, the clinician is typically an experienced psychologist or psychiatrist. However, in the school environment for educational or psychological assessment, the clinician may be a social worker, a visiting psychologist, a speech therapist, a reading specialist, a resource room teacher, a special education teacher, etc. While test administration requires a training program, the proficiency of the clinician is variable especially in the school environment. Each of the assessment tools has extensive instructions for the clinician in the area of question sequencing and scoring related to establishing the critical range of the subject; this is involved with the subject's basals and ceilings which are determined by runs of right or wrong answers within a particular sequence. A rule might be, "if the subject gets two questions wrong in succession, change to sequence 4 and score all of the answers below question x as wrong and above question y as right". To the uninitiated, this might seem counter intuitive; field experience has shown this aspect of test administration and scoring to be most problematic, especially for clinicians with limited assessment background. For example, clinicians tend to be reluctant to "penalize" subjects by not giving credit for correct answers above the ceiling; others show a reluctance to grant unearned credit for incorrect answers below the basal. Other reasons for bias such as social class prejudice or the assumption that shy or disruptive children are learning impaired may be operative. The subjectivity of manual testing precludes true standardized administration. Subjectivity and deviation from test rules can take place during any part of the testing session. Factors may involve the clinician or the subject.

In the traditional test session, the clinician is expected to manually administer the test, record the scores, and assess the subject's response and behavior. In addition, the clinician is expected to compute the scores and sometimes to write a report suggesting learning programs. This is difficult to do well, especially with "difficult" test subjects. In fact, such testing using a human examiner is often not possible for children with attention deficit disorder (ADD) or those too young to focus long enough to be accurately tested.

While clinicians may be very proficient in their respective fields, they may not speak clearly. They are expected to flawlessly recite scripts to the subjects during evaluation. In some cases, the subject is getting the question wrong just because he or she doesn't understand the examiner. In situations with "English as a Second Language" (ESL) subjects the problem is compounded. Sometimes, the reverse problem manifests itself if the clinician has an accent.

Computer software for test scoring and analysis of error patterns is available for manually administered tests. However, it is necessary to manually enter the raw scores into the computer prior to the automated analysis. Also, there is no computer guidance in administrating the test since this is done as an ad-hoc procedure after the test is over.

OBJECTS OF THE INVENTION

Therefore, the objects of the present invention are as follows:

To preclude all possible bias in test administration, thereby achieving complete objectivity;

To provide dynamic linguistic adaptation to accommodate ESL test subjects;

To enhance the validity of the subject's response by utilizing professional voice actors with unsurpassed clarity in every dialect to guarantee that the subject understands what is being asked;

To automatically determine the subject's basals and ceilings, thereby finding the subject's critical range to ensure the proper test administration and scoring;

To improve subject on-task performance by superior computer presentation of test items which has been shown to improve motivation and focus;

To free the clinician to assess the subject's response and behavior by using the multi-media system to take over the test administration function;

To permit cost-effective screening of students by less-trained and less-paid paraprofessionals using computerized testing; this eliminates the inherent bias in the selection process of students for further professional testing;

To use the features of multi-media computer presentation as an audio-visual aid to enhance the clarity and understanding of test items;

To use the computer as an audio-visual aid in presenting sample items to help clarify instructions and model correct responses;

To use computer-based test administration to maintain test standardization by precisely conforming to traditional modes of evaluation;

To provide automated scoring and analysis of error patterns without the manual re-entry of raw scores; and, To utilize animation and other audio-visual techniques inherent to multi-media technology to create new measures (tests) to test subjects in ways they could never be tested before, as well as to test specific cognitive, motor, and other abilities, which could never be tested before.

SUMMARY OF THE INVENTION

The nature and substance of this invention includes a method and system to perform psychological and educational assessment of subjects using multi-media technology.

The method of the present invention for psychological evaluation of human subjects includes the steps of providing a human subject, such as a student, to be evaluated with a multi-media capable computer having a view monitor means, such as a VDT terminal, and a computer input-response means, such as a keyboard, a mouse or a touch screen. A human psychological tester operates the multi-media computer and conducts the psychological evaluation of the student.

To avoid the inherent bias occurring when a tester speaks in a language or dialect not fully comprehended by the student or other human subject, the multi media computer has a linguistic adaptation means, such as a sound card and data associated therewith, which can produce sounds, such as test instructions, in the most appropriate language and dialect of the test taker, such as a student, so that the human tester can provide the human subject with instructions for responding to the psychological evaluation.

The human subject is exposed to computer-generated multi-media psychological evaluative probing, so that the human subject can respond to the computer-generated psychological evaluative probing.

The computer tallies and records the student's responses and analyzes the human subject's recorded responses. Afterward the computer automatically prepares a report based upon the human subject's recorded responses, and transfers its report, such as transfer to a computer-readable diskette or by printing to a printer.

The psychological evaluation of the human subject is provided by at least one software program stored in a randomly accessible non-volatile computer memory, such as the computer's hard drive, for providing at least one type of psychological evaluation. The at least one software program further includes a plurality of discrete audible and/or visual segments such as questions to be responded to by the human subject being evaluated.

The discrete audible segments include audibly-reproducible signals stored in a randomly accessible non-volatile computer memory for producing sounds to be responded to by the human subject being evaluated, such as spoken phrases to be responded to by the human subject. The spoken phrases are selected from a plurality of user-selectable languages and/or dialects.

The discrete visual segments include visually-reproducible signals stored in a randomly accessible non-volatile computer memory for producing images to be responded to by the human subject being evaluated, such as text selected from a plurality of psychological evaluation question items stored as text written in a plurality of languages and/or dialects and/or character sets, such as Chinese or Cyrillic, among others.

To assist in evaluating temporal time oriented tasks, such as allowing a student to decide which of three moving objects, such as balls, moves fastest, or the calculated destination thereof, optionally the discrete visual segments may include computer-generated motion for psycho-motor evaluation of human subjects.

The computer generated motion may include a plurality of user selectable visually-perceived motions, such as the moving balls, at differing speeds and/or velocities and/or accelerations.

Moreover, the linguistic adaptation means includes at least one software program capable of presenting audible psychological probing tasks in a variety of user-selected languages and dialects, wherein the languages and dialects are respectively stored discretely in randomly accessible computer non-volatile memory, such as the computer's hard drive or upon a removable diskette.

The method of using multi-media technology in psychological evaluations may include an evaluation of the human subject's emotional status, mental health, learning ability, neurological impairment status, educational status, educational achievement status, aptitude for future education or aptitude for future vocational education.

In changing the language or dialect of the test, the linguistic adaptation means further includes a user selection of the language and/or dialect to be used for the psychological evaluation of the specific human subject, such as a student.

Furthermore, the linguistic adaptation means further includes information stored in a computer non-volatile memory means, such as discrete randomly accessible test questions in a plurality of languages and/or dialects on the hard drive or insertable diskette of the multi-media computer. To begin the test, the human psychological tester selects the type of psychological evaluation to be conducted and selects the language and/or dialect in which the test is to be conducted. In that manner, the test avoids language based bias in the use of interactive multi-media applications in psychological testing.

BRIEF DESCRIPTION OF THE DRAWINGS

The present invention can best be understood in conjunction with the following drawings, in which:

FIG. 7B is a keyboard detail of the present invention, showing "C", "E" and "I" keys;

DETAILED DESCRIPTION OF THE DRAWINGS

Figure 1:
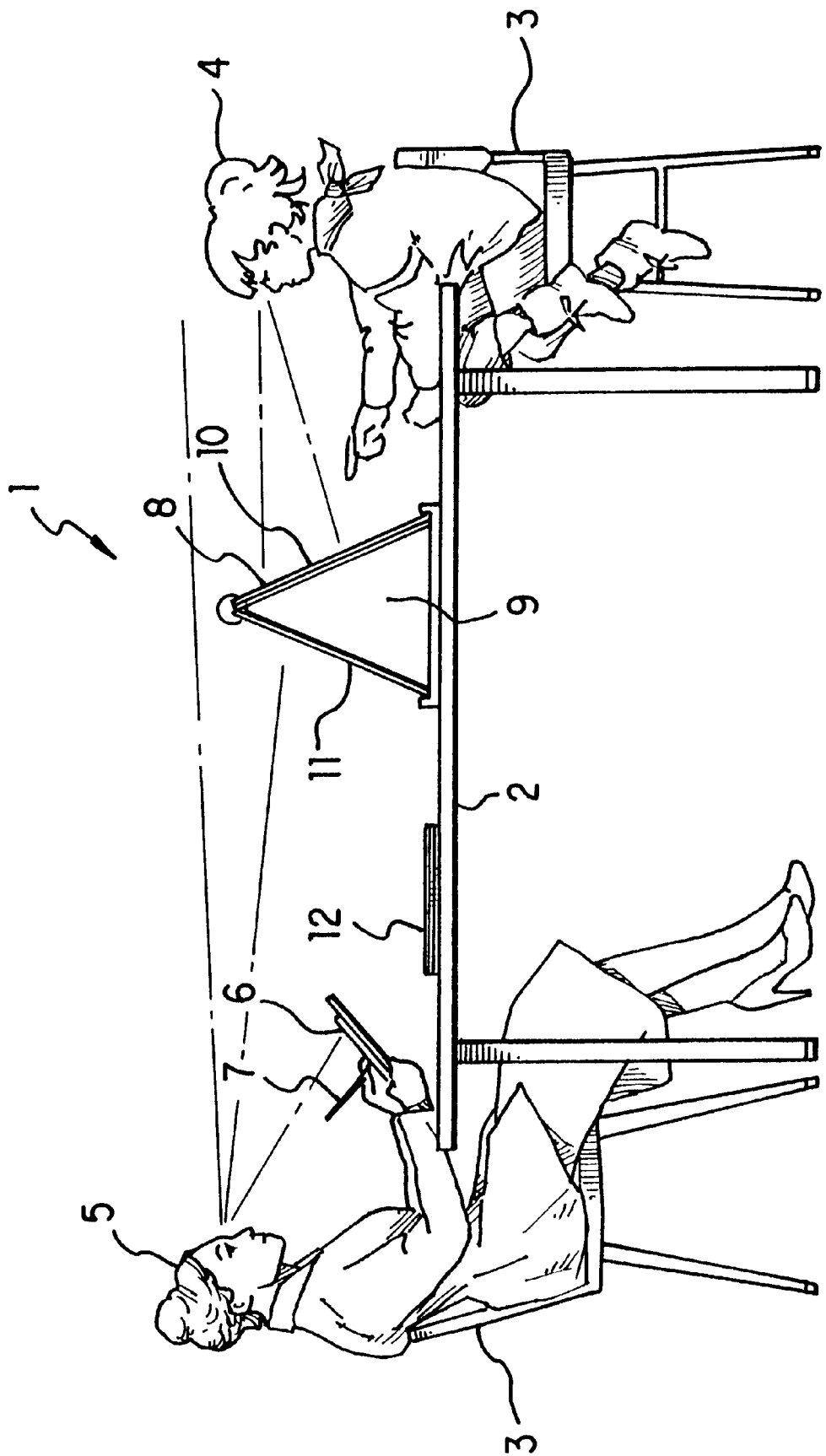
FIG. 1 is a side view of a prior art manual test session.

As shown in FIGS. 1–12A through 12E, a multi-media computerized system for psychological evaluation of a human subject includes a multi-media computer 17 having a view monitor means 21, and a computer input-response means 23, such as keyboard 25, a mouse 18 or other input means.

Figure 7A:
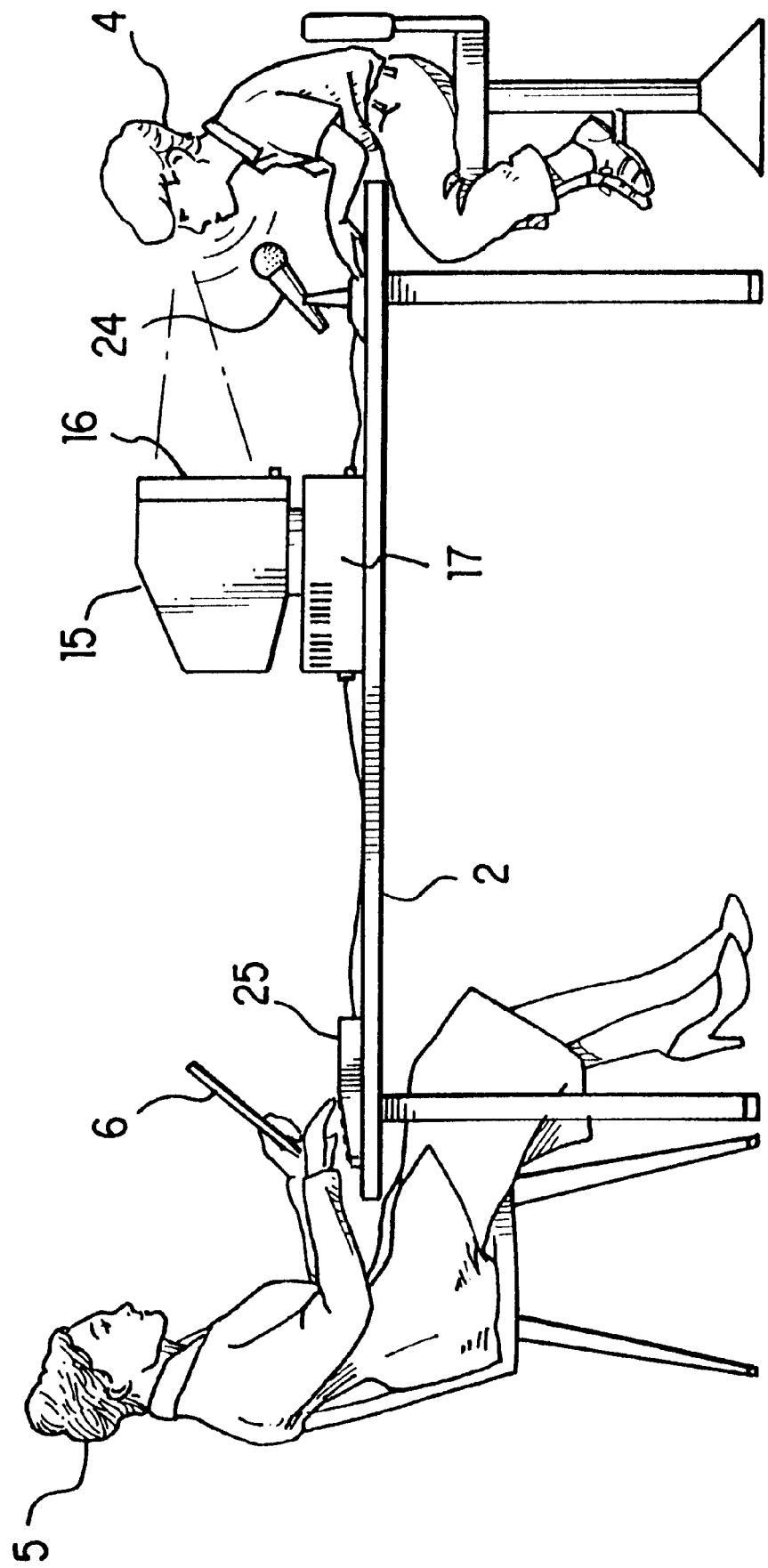
FIG. 7A is a side view of a multi-media session of the present invention, using a voice response mode.

In the preferred embodiment shown in FIG. 7A, input response means 23 is used for a human psychological tester 5 to input communicated sensory data from the human subject 4 to multi-media computer 17 to conduct a psychological evaluation of the human subject 4.

A linguistic adaptation means is provided in computer 17 to avoid the inherent bias occurring when a tester 5 speaks in a language or dialect not fully comprehended by the human subject 4. The linguistic adaptation means includes a library of pre-recorded sets of test instructions in a plurality of language and dialects.

A computer-responsive user selectable means, such as keyboard 25, is provided to allow tester 5 to select at least one set of pre-recorded test instructions in at least one language and dialect thereof appropriate to the language and dialect of human subject 4.

An audible playback means 22 communicates audibly the at least one set of pre-recorded test instructions in the appropriate language and dialect thereof. The audible playback means has a sound card and data associated therewith. The sound card audibly produces audible test instruction sounds, in the appropriate language and dialect thereof.

A software program further includes a plurality of discrete audible and/or visual segments such as questions to be responded to by the human subject being evaluated. The discrete audible segments are included in audibly-reproducible randomly accessible non-volatile computer memory for producing sounds to be responded to by the human subject 4 being evaluated. A user-selectable set of computer-generated multi-media psychological evaluative probing data communicates with the audible playback means 22, and a recording means, such as a microphone 24 records recordable responses of the human subject 4 in response to the computer-generated psychological evaluative probing. A tally means tallies and records the human subject 4's responses.

A computer output printer automatically preparing a written record of the human subject 4's recorded responses in a written report, which report is transferred to a computer readable means, and stored in randomly accessible non-volatile computer memory of multi-media computer 17.

FIG. 1 shows a prior art educational assessment session 1 involving a clinician 5 manually administering an educational assessment test to a student 4. Although both are shown sharing table 2 and seated on chairs 3 facing each other, this may not be a practical position for the clinician 5. The test material 8 is shown in an easel form as is popular; an optional easel holder 9 is shown propping up the material 8 which uses a wire binding facilitating easy lie-flat page manipulation.

In this type of test, the construction of the test is such that the surface 10 facing the student 4 has a panel of pictures while the surface 11 facing the clinician 5 has a precise instructional script to be recited to elicit the answer response from the student. Besides reading the instructional script, the clinician must enter raw scores on the answer forms 12 and take observational notes on pad 6 using pencil 7. The student 4 answers the recited question by pointing to one of the pictures on the panel.

While seated clinician 5 is in a good position to read the instructions 11, make behavioral observations and enter notes on pad 6, it is doubtful whether she can reliably ascertain the object of the pointed finger of student 4 from the position shown.

Therefore, the clinician 5 may be seated at an angle to student 4 to better view his answer. In addition to this activity, the proper administration of the test requires the clinician to be aware of basal and ceiling rules to know when to skip to other question sequences.

Figure 2:
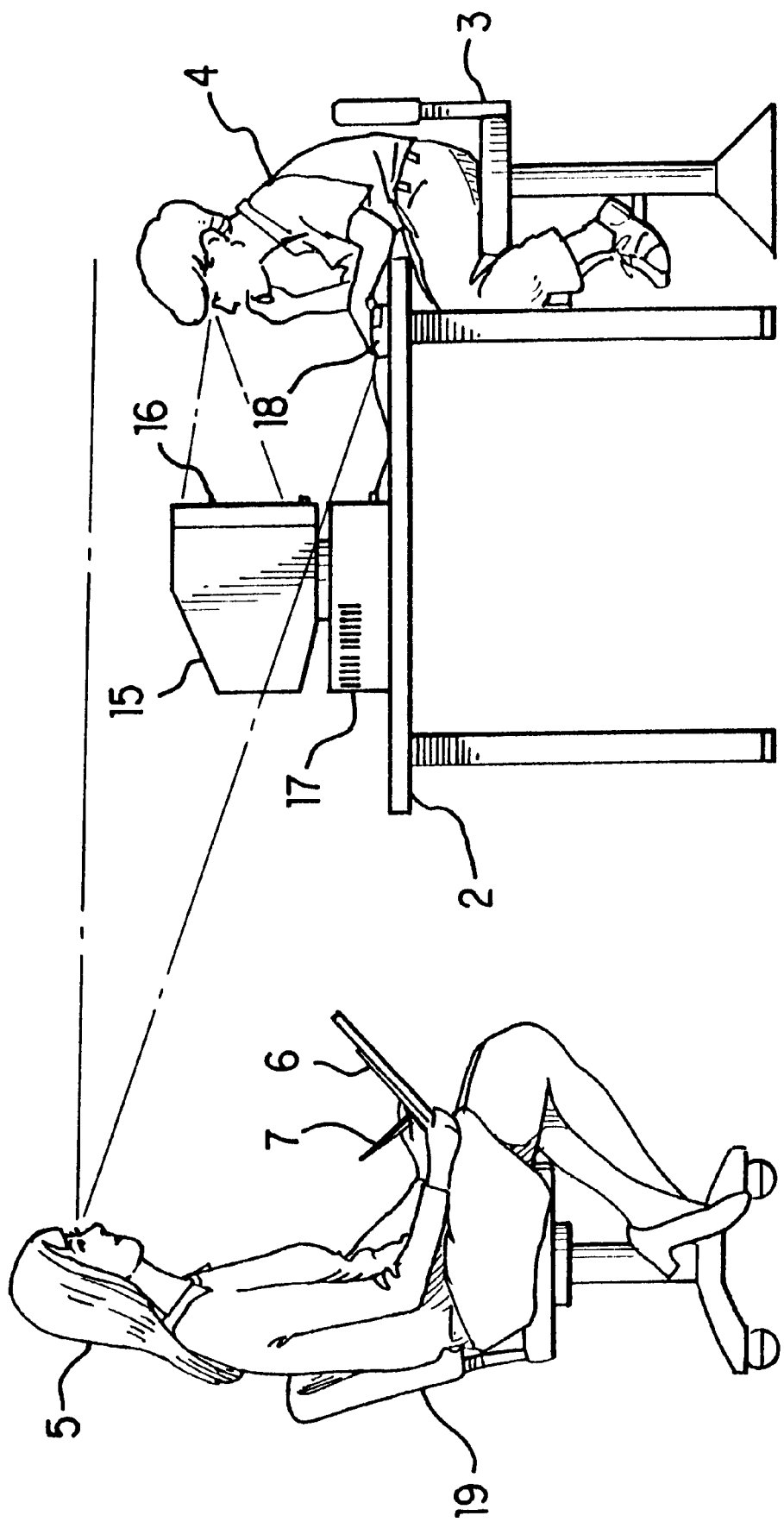
FIG. 2 is a side view of multi-media equipment used in a test session using the present invention.

FIG. 2 shows an educational assessment session of the present invention, using a multi-media system to give the same type of test as had been shown in FIG. 1. Here, the student 4 is seated at table 2 facing screen 16 on video display terminal 15 sitting atop multi-media personal computer 17. He uses mouse 18 as a pointing device to indicate his answer. The clinician 5 is shown sitting on stool 19 free to enter behavioral notes on pad 6 with pencil 7. She can hear the questions being perfectly enunciated by the audio output of the computer 17 and observe the actions of the student 4. She does not have to record answers or recite instructions or questions. An optional seating position for the clinician 5 is to be located behind student 4, since this provides less distraction.

Figure 3:
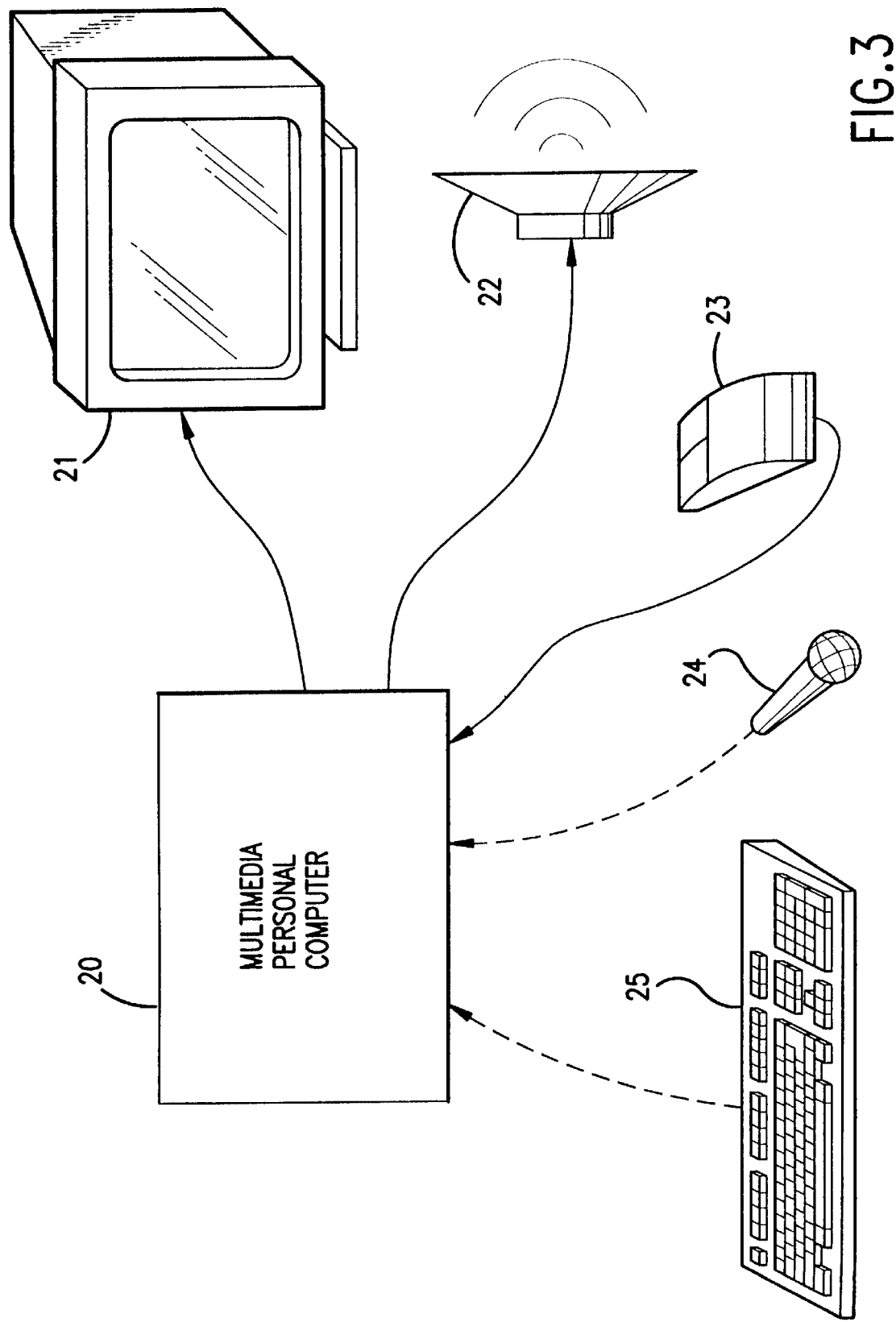
FIG. 3 is a block diagram thereof, showing the essential system components of the multi-media system.

FIG. 3 shows a block diagram of the required elements of a multi-media system for administering psychological and educational assessment tests. A multi-media computer 20 is shown attached to video display terminal 21, loudspeaker 22, and mouse 23. Optional items include microphone 24 and keyboard 25.

Figure 4:
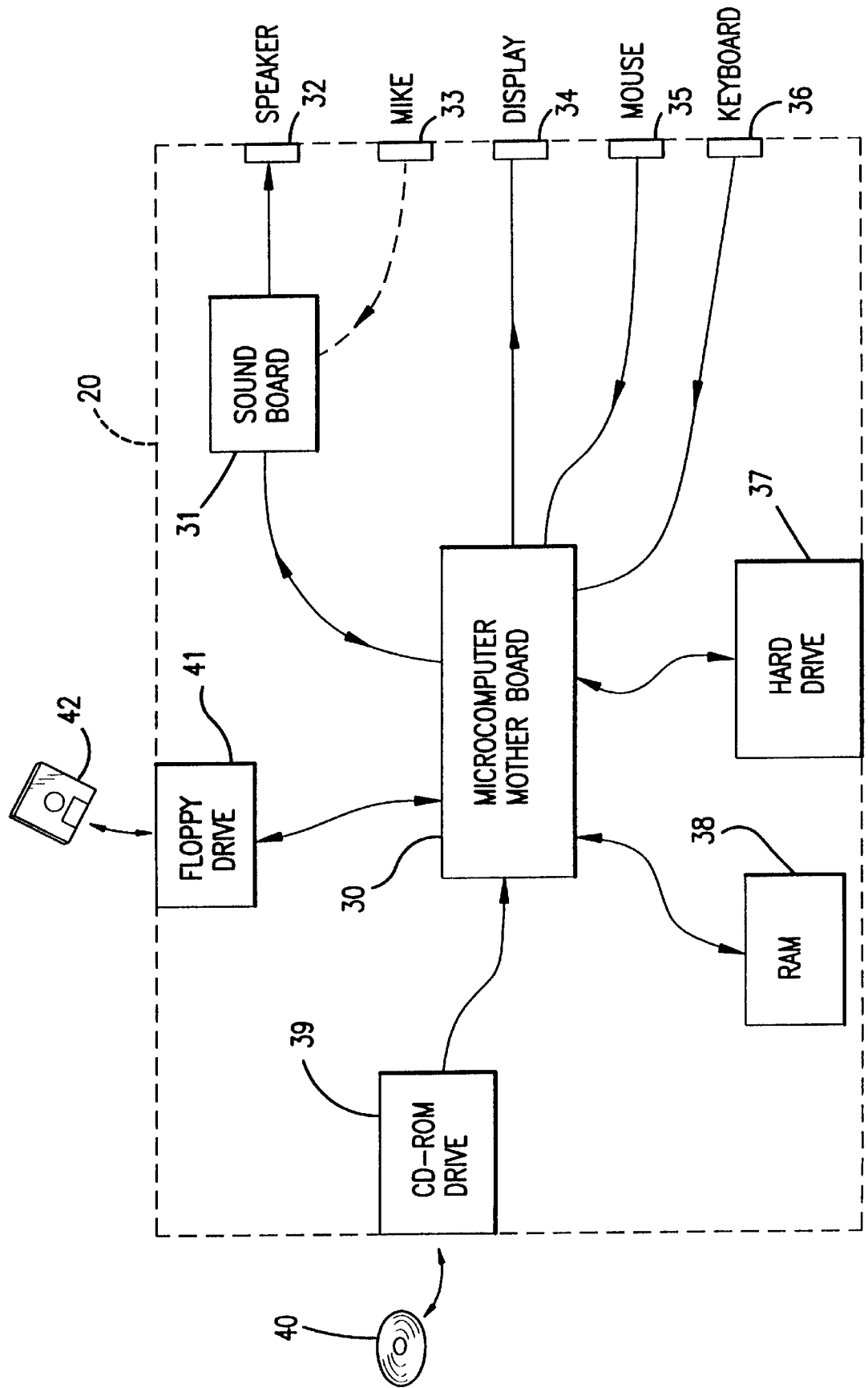
FIG. 4 is a high level block diagram thereof, showing a multi-media personal computer used with the present invention.

The computer 20 may be any of the common multi-media computers as detailed in FIG. 4. These include a mother board 30 containing a microprocessor and other modules and support electronics, with optional extra random access memory (RAM) 38, a hard drive 37, a floppy drive 41 using removable media (diskettes) 42, a CD-ROM 39 with removable CD 40, a sound board 31 and a variety of sockets or ports to support a speaker 32, a microphone 33, a display 34, a mouse port 35 and a keyboard socket 36.

Typical current specifications for the multi-media computer may be those of a Packard Bell model AX3510 which has 8 MB RAM, a 1000 MB hard drive, Quad speed CD-ROM, stereo speakers and an Intel 100 MHZ Pentium processor. Schools are more likely to have older equipment, and these systems could easily be upgraded to serve as a platform for a multi-media assessment test by the addition of an inexpensive ($25 to $30) 8-bit sound board.

The assessment tools of the present invention may run on a 33 MHZ '386 class processor with a 100 MB hard drive, single speed CD-ROM and 4 MB of RAM. A notebook computer having similar capability with integral liquid crystal display (LCD) may also be used as a delivery system.

Any type of pointing device can be used; this includes a mouse, track ball, video game control, joy stick, or even a finger when used with a "touch screen". Other display technologies such as plasma or Texas Instrument's micromirror may be an alternative. These other display technologies also support 3-D presentation displays, which can be used to good advantage in educational assessment tests. For tests requiring only pointing by the subject, neither a microphone nor the keyboard is required. The test software may be entered into the computer as a CD-ROM or as one or more diskettes.

The test content is prepared using state-of-the-art multi-media authoring tools combining audio, picture and text sources. The use of this medium provides an opportunity for many improvements over the manual administration of these assessment tools. For example, the automatic nature of using a computer precludes all possible bias in test administration.

The use of a professional voice actor does not leave enunciation to the chance proficiency of a clinician not trained in this activity. Multilingual capability or dynamic linguistic adaptation is as simple as specifying the language of choice for a particular session; this even accommodates subtle dialect differences in the same language, if desired, by the use of the appropriate voice actor.

The determination of basals and ceilings and the consequent sequencing and scoring are eminently conducive to logical specification and subsequent coding in the software.

It has been shown that computer administration enhances student on-task performance therefore expanding the administration of these assessment tools to some attention deficit disorder (ADD) children and to younger children in general. The use of inexpensive sessions using these educational assessment tools of the present invention via computer with less costly paraprofessional assistants permits their use as a diagnostic tool to screen students in an non-biased fashion.

It is obvious that test standardization is assured by computer administration. What is not obvious is the impact of the change to computer presentation on the validity or reliability of tests that have been normed as a manual tool. Early results from correlation tests presently in progress by a major test provider indicate that norming is not affected by this change to multi-media techniques.

Figure 5A:
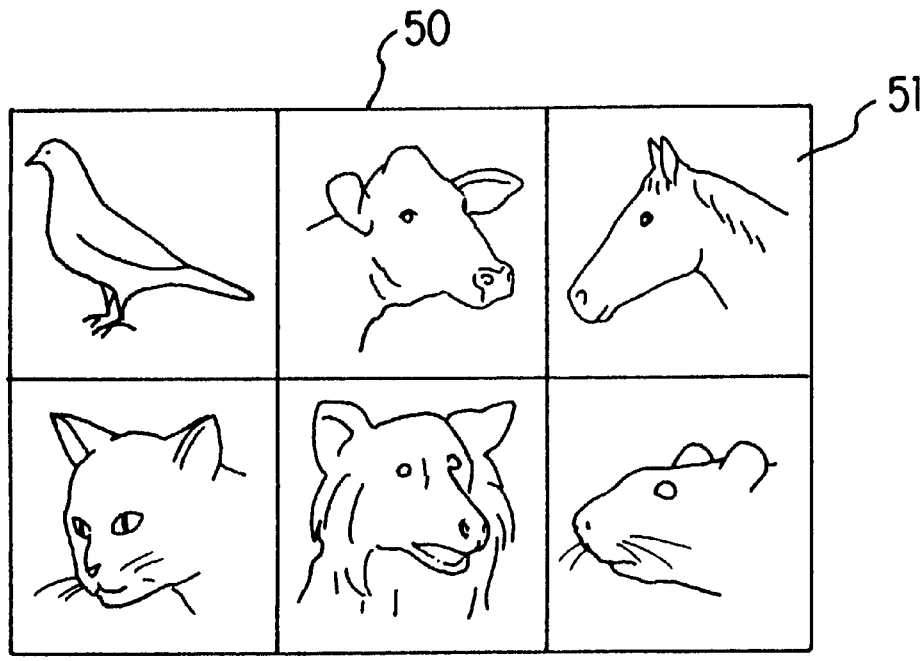
FIG. 5A is a typical video display screen view of a multi-picture panel of the present invention.
Figure 5B:
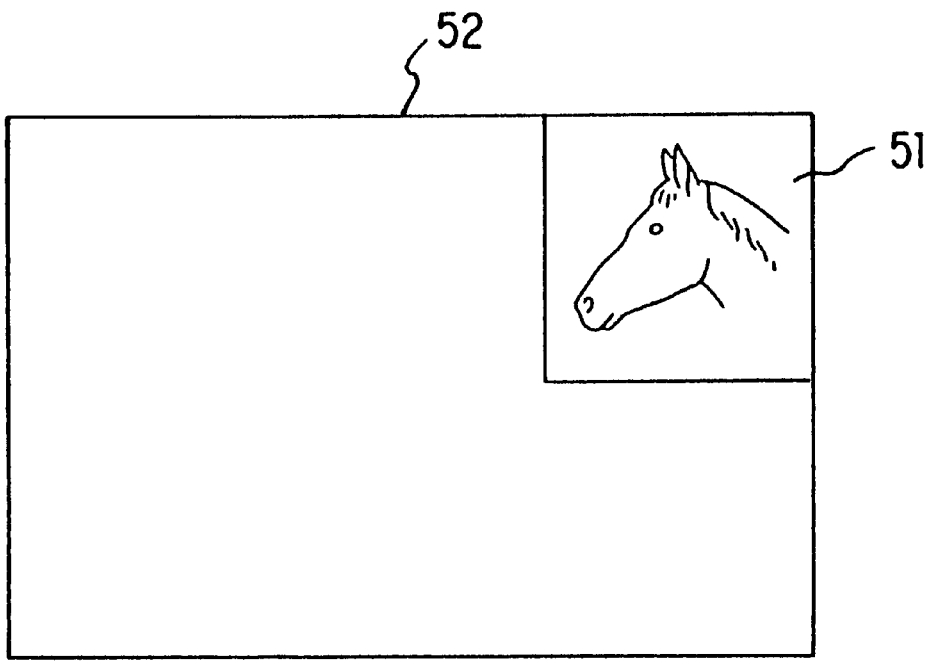
FIG. 5B is a following instructional video display screen of the present invention, bringing attention to a single picture of the previous panel.

The screen view 50 of FIG. 5A shows a typical panel from an assessment test. The upper right panel 51 shows a picture of a horse. Suppose this were the correct answer to a sample question which was incorrectly answered. The computer can easily help clarify the instructions and help model correct responses by presenting the screen 52 of FIG. 5B showing only the horse picture 51 in the same position as in screen 51 but without the "clutter" of the other pictures.

Figure 6:
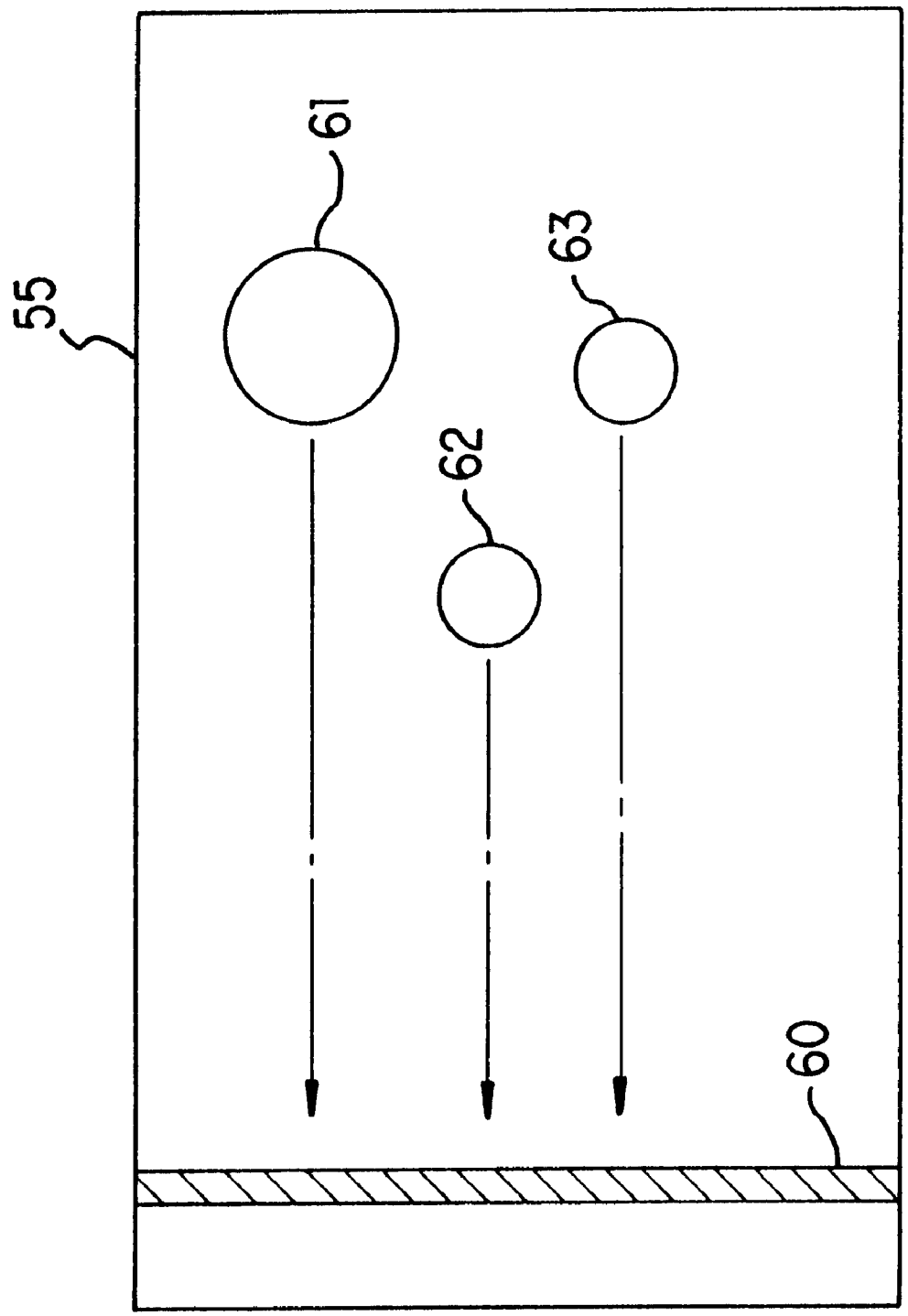
FIG. 6 is a screen panel of the present invention, illustrating the use of animation therein.

FIG. 6 illustrates the use of animation in creating new measures dealing with temporal issues. Screen view 55 is shown with three balls 61, 62 and 63 moving to the left toward wall 60 at different speeds. The question can be, "Point to the ball that went the fastest". Another example of testing cognitive skills involves showing a ball approaching a group of three people. The question could be to predict which person would be hit by the ball. The computer is ideally suited for assessment tools that require the use of timing. In a manual environment, this requires the use of a stopwatch by the clinician to either time the presentation of materials or the period for timed responses (or both). These are illustrations of things that are difficult, cumbersome or impossible to do using a paper technology.

FIG. 7A shows a side view of a testing session using a multimedia computer 17 with an assessment test that requires voice answers by the test subject 4. FIG. 7A shows both a keyboard 25, for use by clinician 5, as well as microphone 24. In actuality only one of these is required during a test session.

In certain embodiments, when computer 17 has voice recognition software of proper quality that it can reliably recognize the utterances of subject 4 without the need for "training", a microphone can be used to field the responses and determine if the answer is right or wrong (or if more than one response has been given). In this case, the clinician can just observe and make notes as she is not involved in answer recognition.

The state-of-the-art of voice recognition software is rapidly improving as witnessed by a product of Syracuse Language Centers which runs on a 386-class computer with 4 MB of RAM and is capable of analyzing the pronunciation of words automatically without training of the software to the respondent's voice.

Standardized tests can be computer administered even when the test requires the student's verbal response.

As shown in FIG. 7A, when the test subject 4 needs to see visual stimuli presented on the video display screen 16, specific keys on the keyboard 25 or buttons on the screen can be used by the examiner 5 to register the response of subject 4 as correct or incorrect, as well as to elicit the appropriate response to the test subject's verbal answer.

When the test subject 4 is not being presented with visual stimuli on the video display screen 16, the screen 16 can be used as an aid to present the scoring criteria to the examiner 5 on a question by question basis. The examiner 5 clicks on options on the screen 16 to evaluate the response of the test subject 4. Different keys on the keyboard 25 can also be linked to specific verbal responses or prompts (i.e. if the test subject 4 gives an ambiguous answer, the examiner 5 can press 'F3' to cause the computer 17 to say 'Explain what you mean').

All the benefits of computer administration of educational assessment are still present: automatic basal and ceiling calculations, clear voice quality, more precise scoring, objective and non-biased administration etc.

One very important advantage is the fact that the present invention enables many more examiners 5 to administer the test bilingually. Perfect fluency in a second language is no longer necessary in order to administer the computer version of that test to test subject 4. If the examiner 5 speaks a 'broken' version of that language, and can sufficiently understand the response of test subject 4, this procedure allows examiner 5 to administer the test with perfectly fluent audio prompts.

The dialect features of the present invention are highly beneficial in that they greatly expand the potential number of qualified examiners 5 who can now test ESL (English as a second language) children, as well as the number of children who can be adequately assessed. It should also be noted that many examiners 5 in the real world have been utilizing 'adhoc', imprecise translations when confronted with an ESL student. In contrast, the procedures of the present invention ensure that the voice is not only professional and native speaking, but that the translations are professionally done as well. This ensures that the validity of the test remains intact.

A less ambitious technique for lesser computers, common in school environments, not utilizing voice recognition software is the "assisted voice recognition" system which uses the keyboard 25 and no microphone 24. In this scenario, three or more keys on the keyboard 25 are mapped onto special functions by the testing software. These are shown with temporary overlays, such as may be bonded with low-tack pressure sensitive adhesive, as "C" 65, "E" 66, and "I" 67 in FIG. 7B which shows a keyboard detail. The clinician must listen for the answer and depress "Correct" key 65, "Error" key 66 or "Invalid" key 67 as appropriate. The computer will correctly score the answer as keyed, but it will emit appropriate audio feedback such as, "Please respond with only one answer" every time one of the Invalid 67 keys is pushed. All other aspects of test administration are still completely automated such as the calculation of basals and ceilings.

Figure 8:
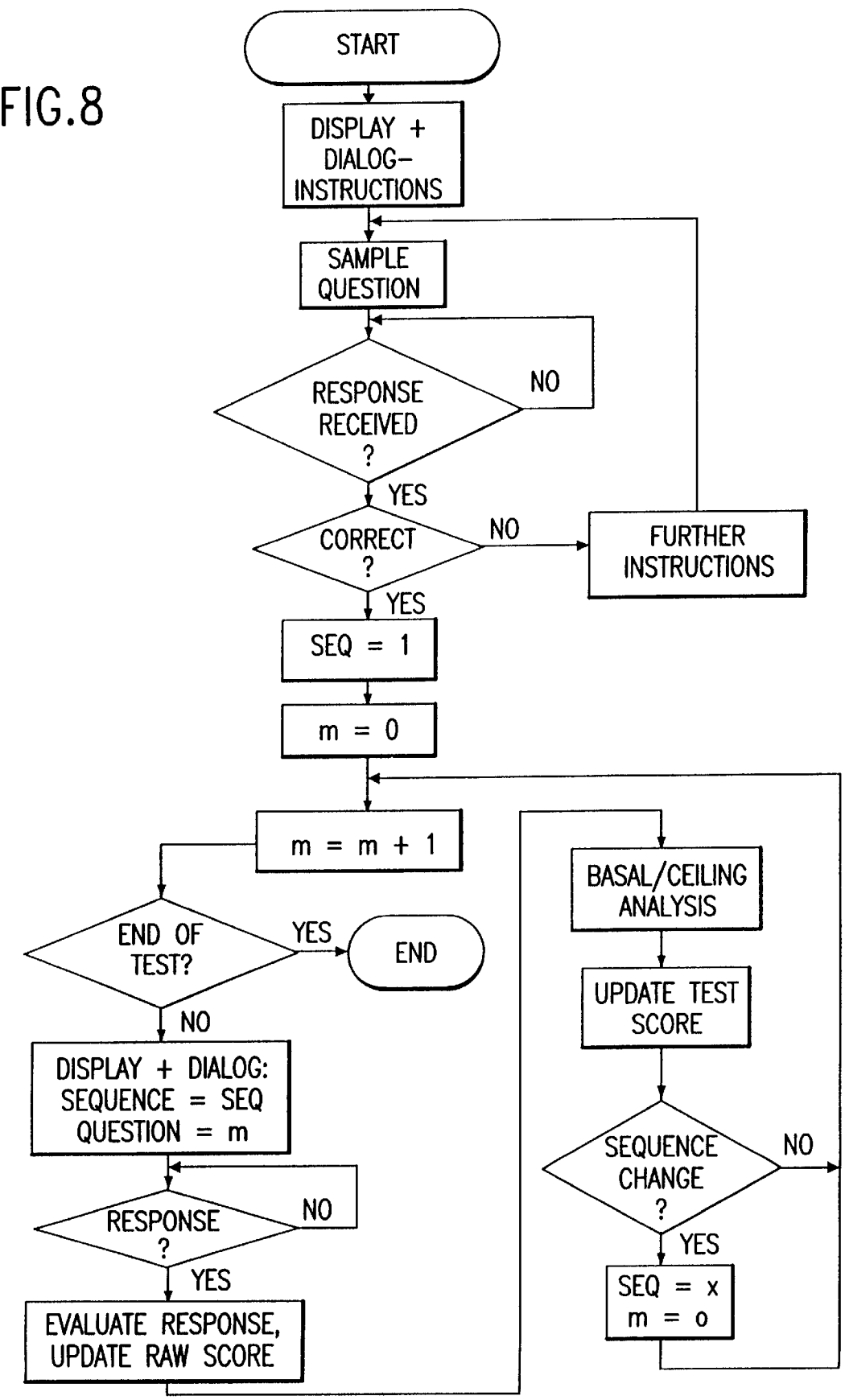
FIG. 8 is a high level program flow chart of the educational test administration of the present invention.

FIG. 8 is a high level flowchart of typical psychological or educational assessment tool software for use on a multi-media system. The program starts with a sample question and can repeat it if it is answered incorrectly. The test can be automatically terminated if the test subject never gets beyond this initial stage. Following the initial sequence and question number setup, an examination of the "end of test" flag is made. Then, a question is presented, the response is examined, the raw score is updated, the basal/ceiling analysis is performed, the test score is updated, the sequence is changed if necessary, and the subsequent following question is presented (or the test is ended). This general flow can be used with pointing as well as verbal answers. It is understood that other logical flows can be used to achieve an equivalent result without deviating from the spirit of this invention.

The remaining FIGS. 9, 10, 11, 12A, 12B, 12C, 12D, and 12E illustrate the features of the present invention with sample video display screens from an educational assessment session.

Figure 9:
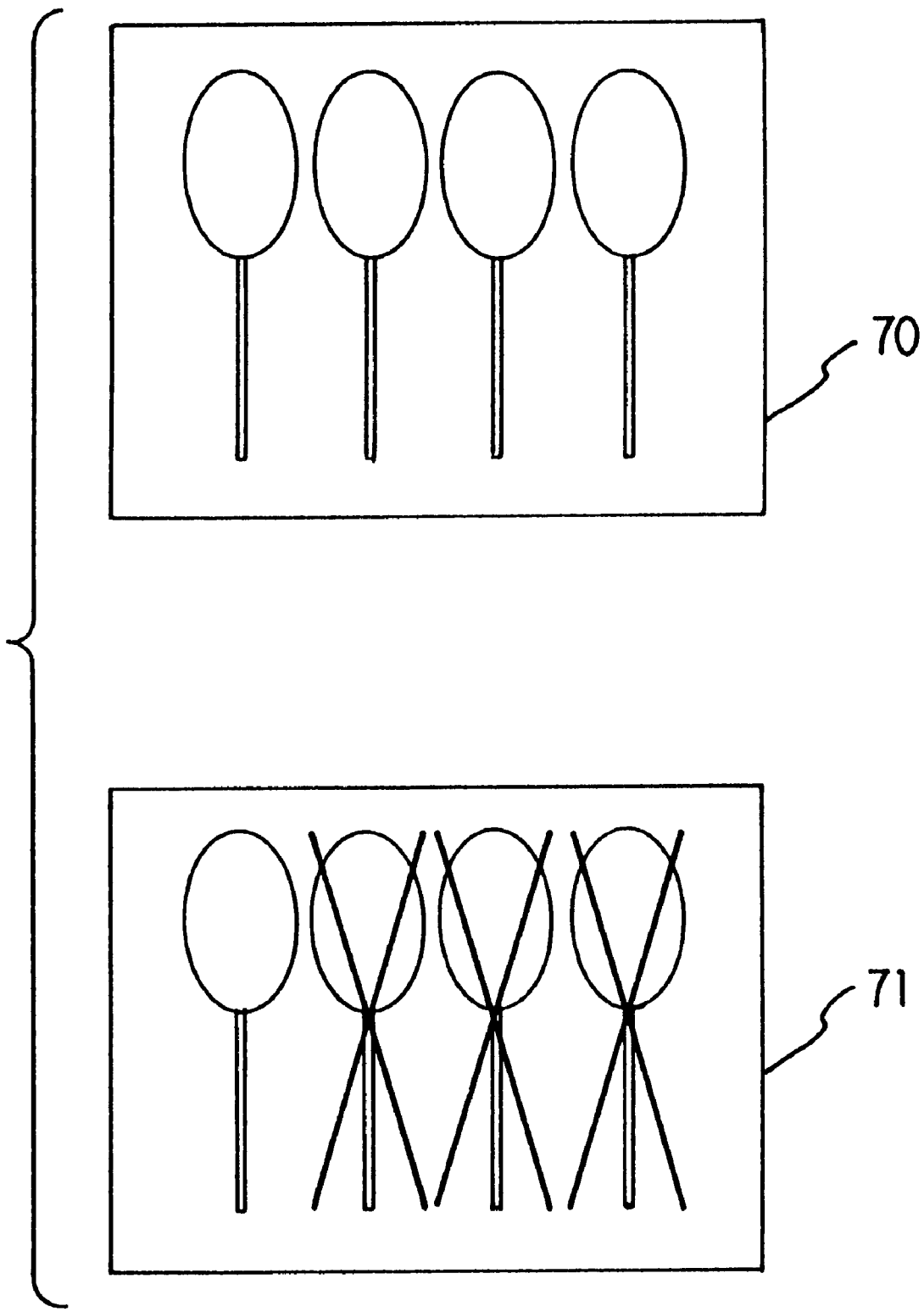
FIG. 9 shows front views of prior art manual test panels.

FIG. 9 shows two question panels, for example, using paper medium, from a prior art manually administered assessment tool. Display panel 70 shows four lollipops. Display panel 71 illustrates the verbal question, "How many lollipops are left if we take three away?". In display panel 71, four lollipops are still shown, but with three of them crossed out.

Figure 10:
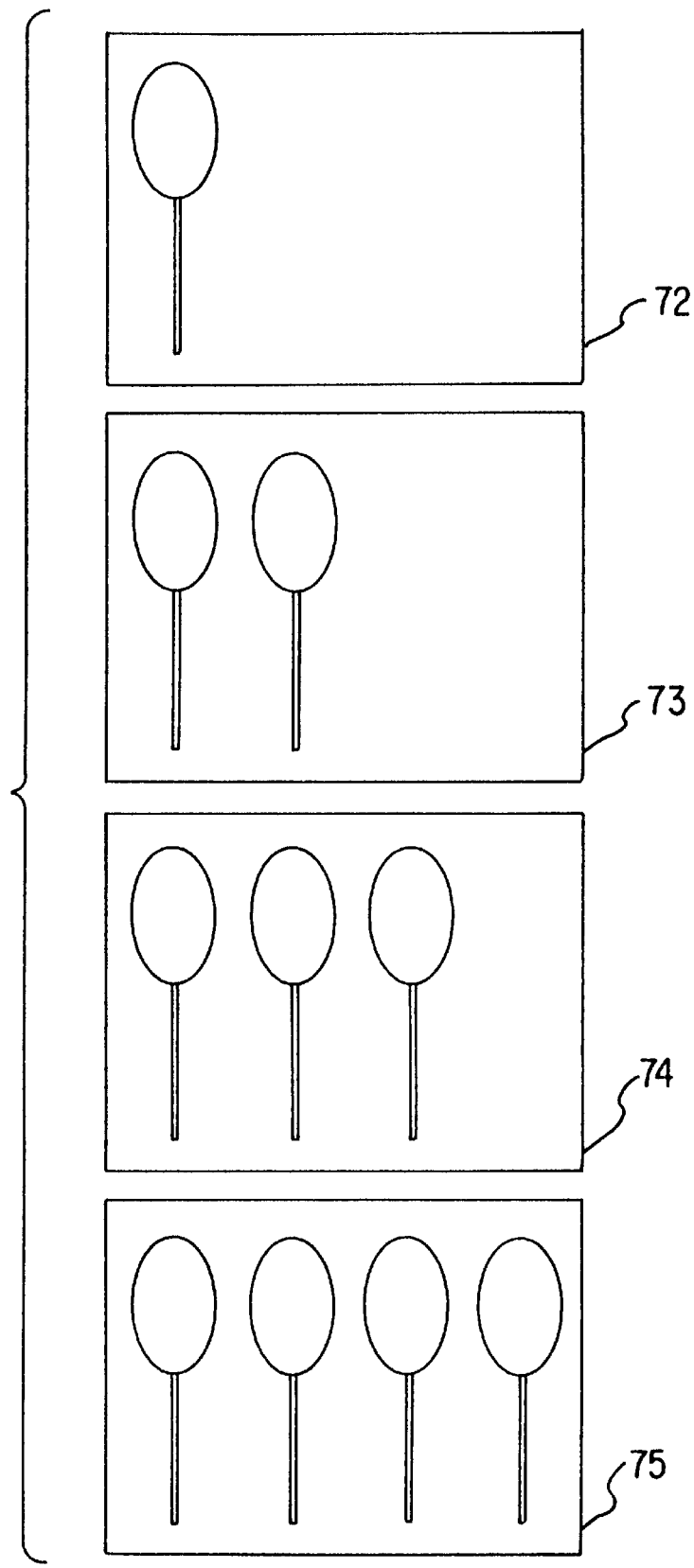
FIG. 10 is a video display screen sequence of the multi-media system of the present invention, shown with clarifying instructions.

Using the multi-media version of the same situation, animation is used to advantage in the sequence shown in FIG. 10. Video display screens 72 through 75 are shown in quick succession with the count "ONE, TWO, THREE, FOUR" on the sound track. Then the reverse sequence shown in video display screens 75, 74, 73, 72, are presented along with the question noted above. This time the test subject doesn't have the confusing picture of the three crossed out lollipops shown in FIG. 9.

Figure 11:
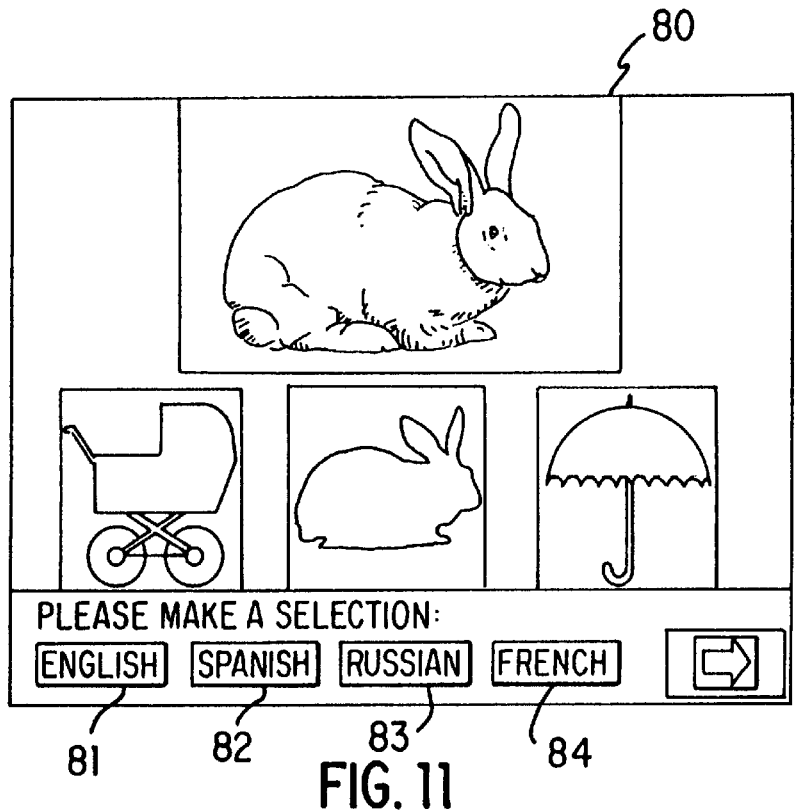
FIG. 11 is a front view of a video display screen, illustrating "Dynamic Linguistic Adaptation" portions of the present invention; and, FIGS. 12A, 12B, 12C, 12D and 12E are front views of video display screens A through E of the multi-media system of the present invention, shown illustrating "Modelling Proper Response" sequences for a sample question.

FIG. 11 shows video display screen panel 80 illustrating the selection of a language for the following multi-media assessment test. This dynamic linguistic adaptation is simply accomplished by using the pointing device to point to the appropriate word, ENGLISH 81, SPANISH 82, RUSSIAN 83 or FRENCH 84. The rest of the session is administered in the language of choice.

Figure 12A:
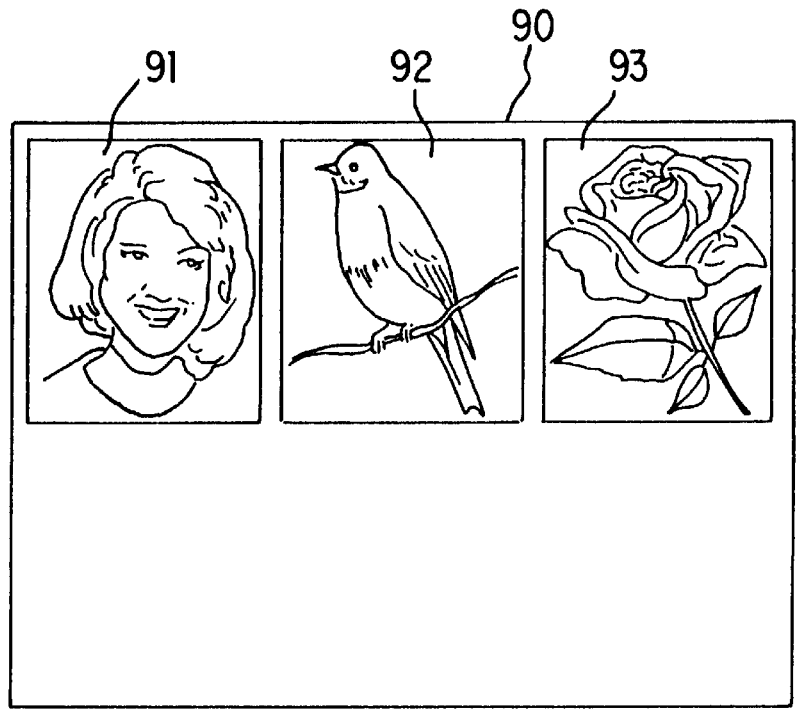
Figure 12C:
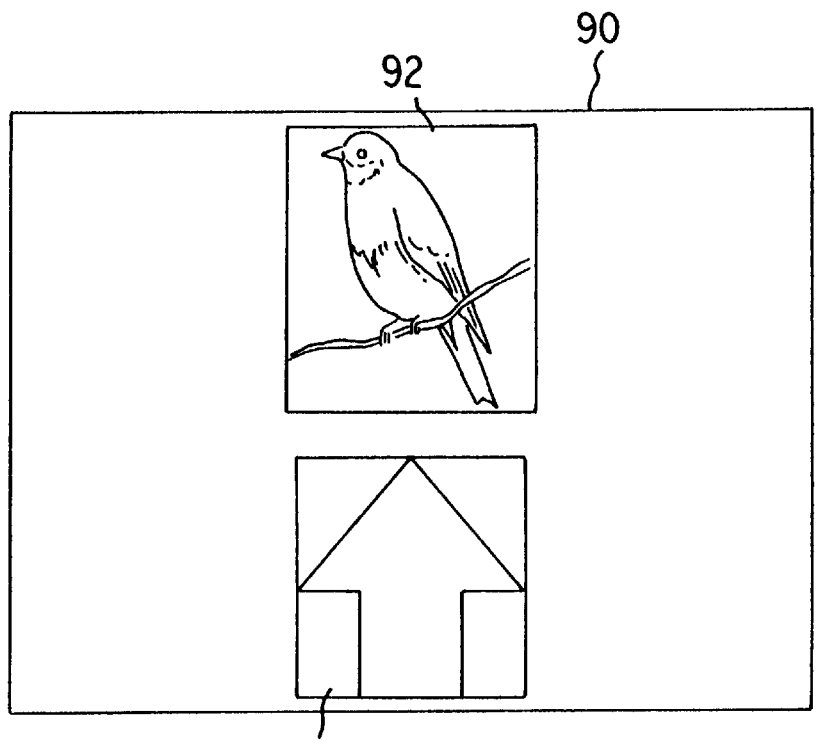
Figure 12B:
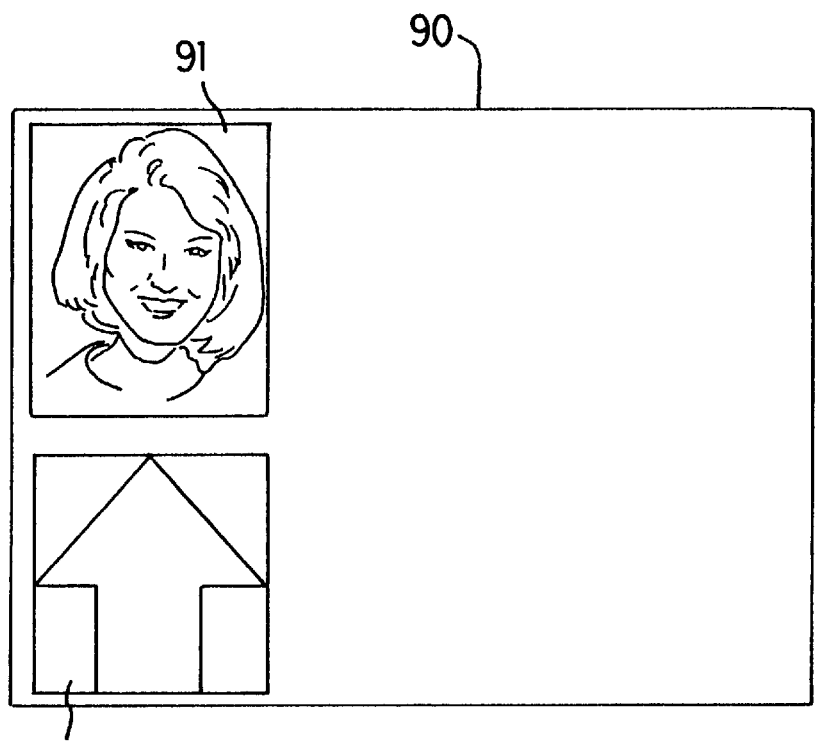

The sequence of screens shown in FIGS. 12A through 12E illustrate the power of multi-media techniques in modelling appropriate responses for sample questions. This is the only area where feedback to the student is permitted. FIG. 12A shows screen 90 with pictures of a girl's head 91, a bird 92 and a flower 93. If the student were asked to point to the girl, and he answered incorrectly, screen 90 shows the image of FIG. 12B showing only the correct answer 91, along with the pointing arrow 94. By not showing the other two images in the same screen, the student's attention is focused on the correct answer.

Figure 12D:
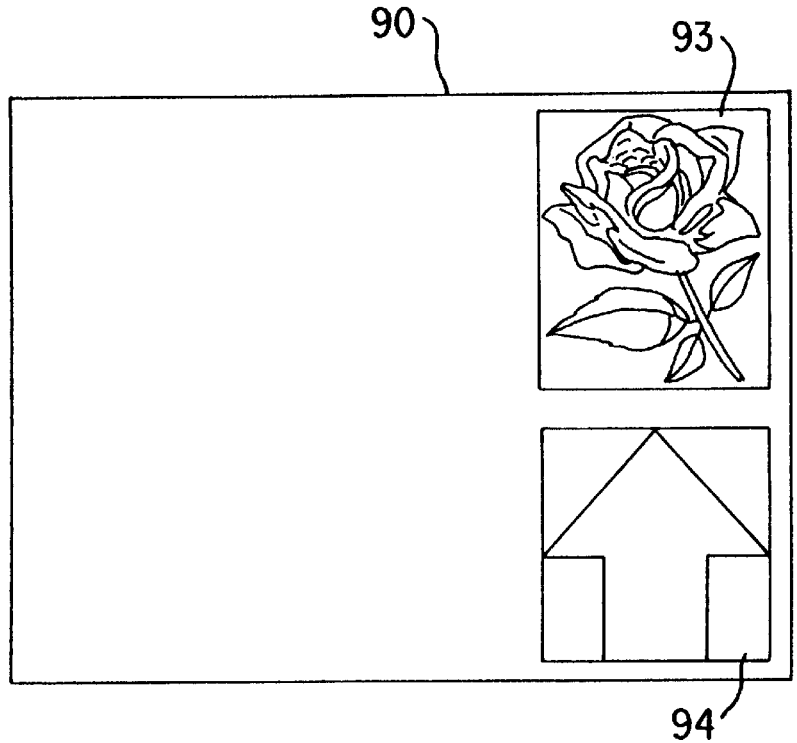
Figure 12E:
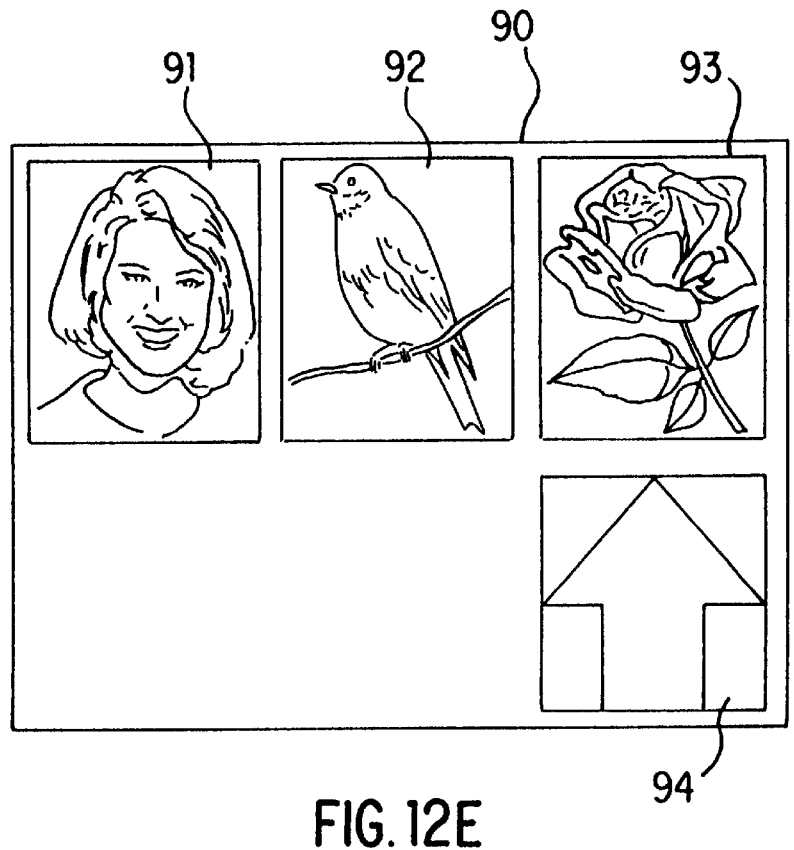

FIGS. 12C and 12D show the video display screen images if the incorrect answer were given in response to questions, asking for the bird 92 picture or the flower 93 picture respectively. In FIGS. 12C and 12D, only a single visual picture 92 or 93 is shown, and it is in the same position as in the initial "three picture" panel. If the incorrectly answered question was asking the student to point to the flower, the sequence of FIGS. 12A, 12D and 12E would be shown to completely model the appropriate answer. The student's attention would be focused on the flower in FIG. 12D and then the flower would be shown in companionship with the other two pictures in FIG. 12E.

OPERATION OF THE INVENTION

The following typical example shows how the method and system of the present invention is used. It is illustrative of one example only. A sample psychological/educational assessment test is run in a computer program designated by Applicant as the "Comprehensive Responsive and Expressive Vocabulary Test-Computer Administered" (CREVT-CA).

Running the CREVT-CA Program

To start the program, the user double clicks on the CREVT-CA icon in the CREVT-CA Program Group. If the user has installed the program in WINDOWS 95®, from the start menu, the user selects "Programs, CREVT Program Group", with the CREVT-CA icon. After the opening title, the Main Menu appears. Six choices on this screen are available to the user, such as:

(OK) Administer Tests
(OK) Score Expressive Subtest
(OK) View a Previous Record
(OK) Change the Password
(OK) Recharging Information
(OK) Exit To choose an option, the user points and clicks on the box next to the operation the user wishes to being.

Administering a Test

To administer a test to an individual, the user chooses "Administer Tests" from the Main Menu.

The Subtest Selection Menu appears. The user cam choose to administer both the Receptive and Expressive subtests or individual subtests. The user clicks on the "OK" button next to the name of the subtest(s) the user likes to administer, such as:

(OK) Receptive Vocabulary Subtest (OK) Expressive Vocabulary Subtest (OK) Both Subtests Then, user the completes the demographic information screen.

The user selects an appropriate language and dialect of the test subject, such as a child, such as "French-Quebecois" vs. "French-Haitian Creole", or "English-Australian" vs. "English-Southern American" and the like. When this is done, the user clicks on the "OK" button to continue.

Finally, the user chooses which form of the test the user would like to administer—Form A or Form B. If the user is administering both subtests, the form selection applies to both subtests.

Receptive Vocabulary Subtest

Whether the user has choosen to administer the Receptive Vocabulary Subtest, or both Subtests, the testing begins with the Receptive subtest. The subject is seated in front of the computer with the mouse in hand (in other test environments, the examiner may input information from the subject, who is tested in a hands-free environment). During the Receptive portion of the test, a voice in a pre-selected language and dialect pronounces a word while the subject views the pictures. In this example, the subject simply uses the mouse to point and click on a picture to indicate an answer.

As soon as a ceiling is reached (when the subject misses two consecutive items in the set of items) the program automatically moves on to the next set of pictures.

During the Receptive subtest, a small left-pointing arrow appears in the lower left corner of the screen. This is the "Repeat a Word" button. If the subject did not hear the word that was said, the user tells the subject to click on the arrow button to have the computer enunciate the word again. The user tries to limit the use of the Repeat button during the administration of the test. The user uses it when the subject has not heard a word, not when the subject does not know what the word means.

If the user is using the CREVT-CA program to administer the Receptive portion of the test but is administering the Expressive portion without the computer's assistance, the user can still have the CREVT-CA compute the standard scores, percentiles, and age equivalents for both subtests together. When the Expressive and Receptive subtests are completed, and after the user has finished the Receptive test on the computer, the user simply clicks on the "yes" button to choose to score the Expressive subtest as well. The CREVT-CA program asks the user to enter the raw score of the Expressive subtest and then computes the Receptive, Expressive, and composite scores.

After the Receptive subtest is completed, the user needs to enter the user's password to be able to view the scores (the password is initially set to "CREVT"). First, the screen displays a graph of the percentage of correct answers per set of pictures. This graph can be printed by clicking on the 'OK' button next to the word "Print" at the bottom of the screen. To continue on and to view the subject's scores, the user clicks on the 'OK' button next to the words "Continue" and "View Test Scores".

Expressive Vocabulary Subtest

The Expressive portion of the test is given on the computer after the Receptive portion or by itself. During the Expressive portion of the test, the computer screen is turned away from the subject and toward the examiner. The computer gives the instructions orally and asks the subject to define a series of words. The examiner listens to the subject's definitions and scores them using the criteria shown on the screen.

A) The Examiner scores the subject as follows:

1. If the subject said one of the phrases listed in the "CORRECT" box, the examiner clicks on the subject's selected phrase in the "CORRECT" box or on the word "CORRECT" at the top of the box. The CREVT-CA program then scores the answer as correct.

2. If the subject said one of the phrases listed in the "QUERY" box, it means that the subject's answer was incomplete or too ambiguous. The examiner clicks on the subject's selected phrase in the "QUERY" box or on the word "QUERY" at the top of the box. The computer asks the subject to tell more about the given word. The subject is given one more chance to give a correct, complete definition.

3. If the subject said an incorrect answer, the examiner clicks on the word "INCORRECT" on the screen. The computer asks the subject more about the given word. Clicking on the word "INCORRECT" produces the same result as clicking on the word "QUERY".

4. If the subject says, "I don't know anything about that word", the examiner clicks on the phrase "I DON'T KNOW", which appears in the "INCORRECT" box on the screen. The program does not ask the subject to tell more about the given word but scores the answer as incorrect.

5. If the subject says a correct answer when asked to tell more about the word (see Situations "2" and "3" above), the examiner scores the subject as correct, as explained in Situation #1 above. If the subject still does not give a complete definition of the word, the examiner clicks on the phrase in the "QUERY" box that the subject said, on the word "QUERY", or on the word "INCORRECT". The answer will then be scored as incorrect.

6. For some questions, the subject needs to say two correct phrases in order to be scored correct. In such a use, the top "CORRECT" box has two headings to choose from: "ONE CORRECT REPLY" and "TWO CORRECT REPLIES". The user clicks on "ONE CORRECT REPLY" if the subject only said one correct phrase and the user wants the computer to ask the subject to tell more about the word. The user clicks on "TWO CORRECT REPLIES" if the subject said two correct phrases from among the choices given. The user can also click on the phrases in the top box to indicate what the subject said. If the subject gave two correct responses, the user simply clicks on the two phrases that the subject said, and the subject will be scored as correct. If the subject only gave one correct response, the user clicks on the correct phrase and then clicks on "QUERY", "INCORRECT", or "I DON'T KNOW". This indicates that the user wants the computer to ask the subject for more information about the word. When the subject says only one correct response and the computer asks for more from the subject, the heading of the top box changes from "ONE CORRECT REPLY" and "TWO CORRECT REPLIES" to "SECOND CORRECT REPLY". To indicate that the subject said a second correct response, the user clicks on the phrase that the subject said, clicks on the words "SECOND CORRECT REPLY", and the subject is scored as correct.

B. Repeating Words:

If the subject did not hear the word that was said, the examiner clicks on the left-pointing arrow ("Repeat") button in the lower left corner to have the computer enunciate the word again in the appropriate language and dialect of the subject. The user limits the use of this button during the administration of the test. It is used when the subject has a word, not when the subject does not know what the word means.

C. The Child's Reply Box:

On the bottom of the screen is the "CHILD'S REPLY" text box. The examiner uses this box to record the answer of the subject. If the examiner clicks on any phrase in the "CORRECT" or "QUERY" boxes, the phase is automatically placed into the "CHILD'S REPLY" text box. The examiner can also type a subject's answer into the text box and edit the phrases entered there. To edit the text, the user drags the cursor over the text to be edited to highlight the text. Then the user hits the Delete key to remove the text or to "drag and drop" the highlighted text to a new location within the reply box.

D. The "Continue" Button:

At the end of each question, the examiner clicks on the right-pointing arrow "Continue" button to indicate that the "CHILD'S REPLY" text box contains whatever information should be saved in the subject's record and that the subject is ready to continue.

E. End of the Subtest:

The Expressive Subtest automatically ends when either a ceiling is reached (i.e., when the subject misses three consecutive items) or when the last (25th) item is administered.

Viewing Score and Producing Reports

A) Viewing and Printing the Scores After Administering a Test:

When the testing is finished for a particular subject, the examiner enters a password (the password is initially set to "CREVT") to view a comprehensive report of the test results on the computer screen. The examiner can then print out a hard copy of the report by clicking on the "PRINT" button at the bottom of the scores screen. If the Expressive subtest was administered and some information was saved in the "SUBJECT'S REPLY" text boxes, the examiner has the option of also printing out those replies.

B. Graphing Standard Scores:

The CREVT-CA program also allows the user to graph the standard scores obtained by the subject, along with up to seven standard scores with means of 100 and standard deviations of 15 obtained when using other tests with the subject. The examiner thus can compare how the subject scored on the CREVT to how he or she scored on other comparable tests. To produce this graph, the user clicks on the "VIEW GRAPH" button at the bottom of the scores screen. To print, the user clicks on the "OK" button next to the work "PRINT" on the bottom of screen displaying the graph. Clicking on the "OK" button next to the word "Continue" on the bottom of the screen displaying the graph returns the user to the Main Menu.

C. Viewing Previous Scores:

To view the scores of a subject who took the test previously, the user chooses to view a previous record option from the Main Menu. The user enters the name of the subject whose record the user wants to see. The user can search for a record by last name only or by first and last names. The user can also choose to view the database record by record. Once the desired record is displayed on the screen, the user can choose to view either the subject's scores or the subject's responses to the Expressive Vocabulary subtest. The user can also print out hard copies of either of these items.

Exiting the CREVT-CA Program

To exit the program and go back to the user's WINDOWS® session, the user chooses the "EXIT" option from the Main Menu.

If, for some reason, the user wants to exit out of the test during the actual administration of the test, the user can press the Escape key to cancel the test administration. The Escape key only functions during the actual questions of the test. It does not function while any audio is playing or while a sample question of the Receptive subtest is being shown. When the user cancels, no information or scores are saved in the database. The CREVT-CA program is then closed, and the user returns to the WINDOWS® session.

As a result, the user is able to administer a comprehensive psychological/educational assessment test in a dialect-correct environment, in the languages and dialect of the subject, such as a child or an adult.

It is known that other modifications may be made to the present invention, without departing from the scope of the invention, as noted in the appended claims.

I claim:

1. A method of psychological evaluation of human subjects such as a child, an adult or a brain damaged adult, said method comprising the steps of:

a. providing a human subject to be evaluated with a multi-media capable computer having view monitor means and computer input-response means;

b. providing a human psychological tester to operate said computer and conduct the psychological evaluation;

c. providing said multi-media computer with linguistic adaptation means;

d. displaying perceivable instructions to the human subject for responding to the psychological evaluation;

e. exposing the human subject to computer-generated multi-media psychological evaluative probing;

f. permitting the human subject to respond to the computer-generated psychological evaluative probing;

g. having said computer tally and record the responses provided by the human subject; and h. having said computer analyze the human subject's recorded responses;

i. having said computer prepare a report based upon the human subject's recorded responses; and j. having said computer suitably transfer its report, such as by a computer-readable diskette, or by printing to a printer.

2. The method of claim 1, wherein the psychological evaluation of the human subject is provided by at least one software program stored in randomly accessible non-volatile computer memory for providing at least one type of psychological evaluation.

3. The method of claim 2 wherein said at least one software program further comprises a plurality of discrete audible and/or visual segments comprising questions to be responded to by the human subject being evaluated.

4. The method of claim 3 wherein said discrete audible segments comprise audibly-reproducible signals stored in randomly accessible non-volatile computer memory for producing sounds to be responded to by the human subject being evaluated.

5. The method of claim 4 wherein said discrete audible segments comprise spoken phrases to be responded to by the human subject being evaluated.

6. The method of claim 5 wherein said spoken phrases are selected from a plurality of user-selectable languages and/or dialects.

7. The method of claim 6 wherein said discrete visual segments comprise visually-reproducible signals stored in randomly accessible non-volatile computer memory for producing images to be responded to by the human subject being evaluated.

8. The method of claim 7 wherein said discrete visual segments comprise text selected from a plurality of psychological evaluation question items stored as text written in a plurality of languages and/or dialects and/or character sets, such as Chinese or Cyrillic without being limited thereto.

9. The method of claim 7 wherein said discrete visual segments comprise computer-generated motion images.

10. The method of claim 9 wherein said discrete visual segments comprise computer-generated motion images for psycho-motor evaluation of human subjects.

11. The method of claim 10 wherein said computer generated motion images comprises a plurality of user selectable visually-perceived motion images.

12. The method of claim 11 wherein said plurality of motion images comprises images of objects traveling at differing respective speeds and/or velocities and/or accelerations.

13. The method of claim 1, wherein said linguistic adaptation means comprises at least one software program capable of presenting audible psychological probing tasks in a variety of user-selected languages and dialects.

14. The method of claim 13 wherein said languages and dialects are respectively stored discretely as signals in randomly accessible computer non-volatile memory.

15. The method of claim 1 wherein the psychological evaluation comprises an evaluation of the human subject's emotional status.

16. The method of claim 1 wherein the psychological evaluation comprises an evaluation of the human subject's mental health.

17. The method of claim 1 wherein the psychological evaluation comprises an evaluation of the human subject's learning ability.

18. The method of claim 1 wherein the psychological evaluation comprises an evaluation of the human subject's neurological impairment status.

19. The method of claim 1 wherein the psychological evaluation comprises an evaluation of the human subject's educational status.

20. The method of claim 1 wherein the psychological evaluation comprises an evaluation of the human subject's educational achievement status.

21. The method of claim 1 wherein the psychological evaluation comprises an evaluation of the human subject's aptitude for future education.

22. The method of claim 13 wherein the psychological evaluation comprises an evaluation of the human subject's aptitude for future vocational education.

23. The method of claim 13 wherein said linguistic adaptation means further comprises user selectable computer input of said language and/or dialect to be used for the psychological evaluation of a specific human subject.

24. The method of claim 23 wherein said linguistic adaptation means further comprises computer non-volatile memory means comprising discrete randomly accessible test questions in a plurality of languages and/or dialects.

25. The method of claim 13 wherein the human psychological tester selects the type of psychological evaluation to be conducted and selects said language and/or dialect in which the test is to be conducted.

26. A multi-media computerized system for psychological evaluation of a human subject such as a child, adult or brain damaged adult, said system comprising:

a multi-media computer having a view monitor means, and a computer input-response means, said input-response means being provided for a human psychological tester to input communicated sensory data from the human subject to said multi-media computer, to conduct a psychological evaluation of the human subject, a linguistic adaptation means to avoid the inherent bias occurring when a tester speaks in a language or dialect not fully comprehended by the student or other human subject, said means comprising a computer readable library of pre-recorded sets of audible test instructions in a plurality of language and dialects, a user selectable means for selecting at least one set of pre-recorded test instructions in at least one language and dialect thereof, an audible playback means for communicating audibly said at least one set of pre-recorded test instructions in said at least one language and dialect thereof, said audible playback means having a sound card and data associated therewith, said sound card audibly producing audible test instruction sounds, in said at least one language and dialect thereof, at least one software program further including a plurality of discrete audible and/or visual segments such as questions to be responded to by the human subject being evaluated, said discrete audible segments including audibly-reproducible randomly accessible non-volatile computer memory for producing sounds to be responded to by the human subject being evaluated, a user-selectable set of computer-generated multi-media psychological evaluative probing data communicating with said audible playback means, and a recording means for recording recordable responses of the human subject in response to the computer-generated psychological evaluative probing;

a tally means tallying and recording the test taker's responses, a computer output printing means for automatically preparing a written record of the human subject's recorded responses in a written report, and a transfer means for transferring said report to a computer readable means, said report stored in randomly accessible non-volatile computer memory of said multi-media computer.

* * * * *